United States Patent
Moreau et al.

(10) Patent No.: US 10,667,851 B2
(45) Date of Patent: Jun. 2, 2020

(54) PROSTHETIC STERNUM DEVICE WITH MANUBRIUM

(71) Applicant: NEURO FRANCE IMPLANTS, La Ville-aux-Clercs (FR)

(72) Inventors: Patrice Moreau, Boursay (FR); Elie Fadel, Antony (FR); Olaf Mercier, Fontenay aux Roses (FR); Dominique Fabre, Garches (FR); Sacha Mussot, Paris (FR); Karin Worner, Epulsay (FR)

(73) Assignee: Neuro France Implants, La Ville-aux-Clercs (FR)

( * ) Notice: Subject to any disclaimer, the term of this patent is extended or adjusted under 35 U.S.C. 154(b) by 183 days.

(21) Appl. No.: 15/551,892

(22) PCT Filed: Feb. 17, 2016

(86) PCT No.: PCT/FR2016/050362
§ 371 (c)(1),
(2) Date: Aug. 17, 2017

(87) PCT Pub. No.: WO2016/135395
PCT Pub. Date: Sep. 1, 2016

(65) Prior Publication Data
US 2018/0036052 A1    Feb. 8, 2018

(30) Foreign Application Priority Data

Feb. 24, 2015 (FR) ...................................... 15 51572
Jan. 13, 2016 (FR) ...................................... 16 50272
Jan. 13, 2016 (FR) ...................................... 16 50273

(51) Int. Cl.
*A61B 17/80* (2006.01)
*A61B 17/82* (2006.01)
(Continued)

(52) U.S. Cl.
CPC ...... *A61B 17/8076* (2013.01); *A61B 17/8023* (2013.01); *A61B 17/8042* (2013.01); *A61B 17/823* (2013.01); *A61B 17/846* (2013.01)

(58) Field of Classification Search
CPC .............. A61B 17/8076; A61B 17/823; A61F 2/30756; A61F 2/30988; A61F 2/3804; A61F 2/4241; A61F 2/4261
See application file for complete search history.

(56) References Cited

U.S. PATENT DOCUMENTS 4,554,915 A * 11/1985 Brumfield .......... A61B 17/6425
606/54
4,593,698 A * 6/1986 Athans ............... A61B 5/04085
600/386

(Continued)

FOREIGN PATENT DOCUMENTS

FR        3 004 337 A1   10/2014

*Primary Examiner* — Nicholas W Woodall
(74) *Attorney, Agent, or Firm* — Craft Chu PLLC; Andrew W. Chu

(57) ABSTRACT

A prosthetic sternum device with a manubrium includes a plate and a device for attachment to ribs. Each of the devices for attachment to ribs includes an end for rigid connection to the plate and an end provided with a device for engaging with a rib. The plate further includes, in the upper region of same, two elements. Each element rigidly connects a pin and includes a polyaxial joint shaped to allow the multidirectional mobility of the pin.

12 Claims, 2 Drawing Sheets

(51) Int. Cl.
*A61B 17/84* (2006.01)
*A61F 2/30* (2006.01)

(56) References Cited

U.S. PATENT DOCUMENTS

| | | | | |
|---|---|---|---|---|
| 6,132,467 A * | 10/2000 | Keller | ............... | A61F 2/30 |
| | | | | 623/18.11 |
| 8,123,747 B2 * | 2/2012 | Hajianpour | ........ | A61B 17/6491 |
| | | | | 606/54 |
| 8,628,530 B2 * | 1/2014 | Hajianpour | .......... | A61B 17/171 |
| | | | | 606/54 |
| 2013/0158608 A1 | 6/2013 | Viola | | |
| 2014/0257291 A1 | 9/2014 | Houff | | |
| 2018/0193073 A1 * | 7/2018 | Frank | ............... | A61B 17/8076 |

* cited by examiner

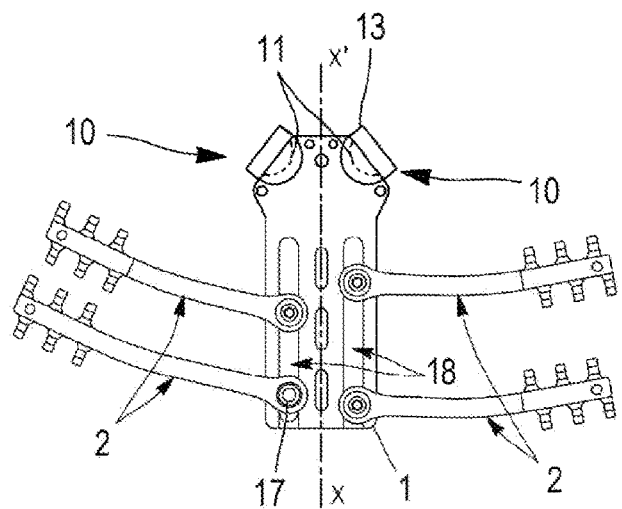
FIG. 4
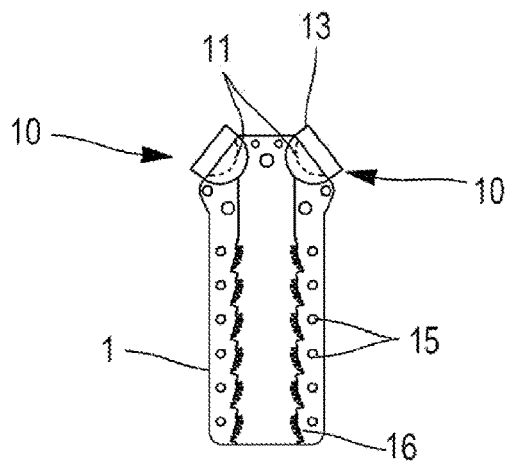
FIG. 5
FIG. 6
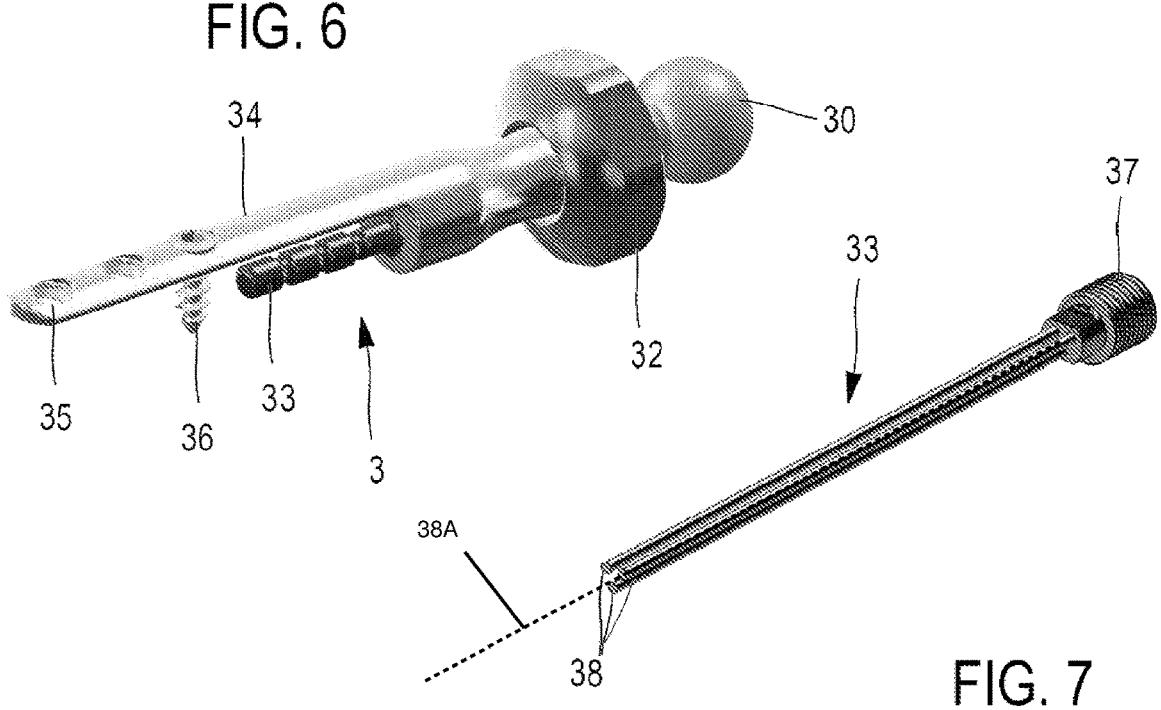
FIG. 7

PROSTHETIC STERNUM DEVICE WITH MANUBRIUM

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to a prosthetic sternum device with manubrium, intended to be implanted to replace a sternum and its manubrium, i.e., the upper part on which the clavicles are articulated.

2. Description of Related Art Including Information Disclosed Under 37 CFR 1.97 and 37 CFR 1.98

A prosthetic sternum device is already known from document FR 3,004,337 including a plate and means for attaching to ribs, where each of said means for attaching to ribs comprises an end for securing to said plate and an end provided with a means for attaching to a rib, said plate including fastening zones of one of said attaching means, distributed on the periphery, on either side of the median zone.

Although such a prosthetic sternum device constitutes progress relative to the prior art when replacing a sternum, it nevertheless has a drawback due to the fact that, upon ablation of the sternum, it is not possible to connect the clavicles, since the manubrium has also been removed.

BRIEF SUMMARY OF THE INVENTION

The present invention aims to improve the prosthetic sternum device according to document FR 3,004,337.

The prosthetic sternum device with manubrium according to the invention includes a plate and means for attaching to ribs, where each of said means for attaching to ribs comprises an end for securing to said plate and an end provided with a means for attaching to a rib, and is characterized in that said plate further includes, in its upper region, two securing elements each for a pin, which each consist of a polyaxial articulation configured to allow multidirectional mobility of said pin.

According to one additional feature of the prosthetic device according to the invention, it further includes two pins, each secured to a polyaxial articulation, and intended to fasten a clavicle or clavicle part, which may or may not be prosthetic.

According to another additional feature of the prosthetic device according to the invention, the polyaxial articulation consists of a ball and socket joint.

According to one particular embodiment of the prosthetic device according to the invention, each pin is intended to be secured to the plate by one end to an element of the polyaxial articulation.

According to another particular embodiment of the prosthetic device according to the invention, each pin is intended to be secured to the plate by one end, said end consisting of an element of the polyaxial articulation.

According to one additional feature of the prosthetic device according to the invention, each of the two polyaxial articulations comprises:
- an extension protruding from the plate, provided with a hemispherical cavity, with an axis passing through the plane of said plate and forming an angle with the main longitudinal axis of said plate, such that said cavity opens outwardly, upwardly and laterally,
- a spherical head intended to be housed in said cavity,
- a cover able to be secured to said extension, intended to close said cavity by enclosing said spherical head, and including an opening allowing a pin to be connected to said spherical head.

According to one additional feature of the prosthetic device according to the invention, each extension includes a housing lined with an insert that includes the cavity.

According to one additional feature of the prosthetic device according to the invention, the outer wall of the insert is spherical, concentric to the cavity, while the housing of the extension is partially spherical, congruent with said insert, so as to create a ball and socket connection.

According to another additional feature of the prosthetic device according to the invention, the insert and the spherical head are made from PEEK.

According to another additional feature of the prosthetic device according to the invention, each pin includes a diaphyseal nail as well as a small plate that extends parallel to said diaphyseal nail, across and at a distance from the latter so as to be able, after insertion of said diaphyseal nail into the clavicle, to come outwardly into contact with this clavicle, said small plate being pierced with at least one hole allowing the passage of the screw intended to be screwed into the bone.

According to one additional feature of the prosthetic device according to the invention, the diaphyseal nail is made up of three parallel rods arranged in a triangle around a central axis.

BRIEF DESCRIPTION OF THE SEVERAL VIEWS OF THE DRAWINGS

The advantages and features of the prosthetic sternum device with manubrium according to the invention will emerge more clearly from the following description relative to the appended drawing, which shows non-limiting embodiments thereof.

In the appended drawing:

FIG. 4 shows a planar schematic view of an alternative of the prosthetic sternum device with manubrium according to the invention.

FIG. 5 shows a partial schematic planar view of another alternative of the prosthetic sternum device with manubrium according to the invention.

FIG. 6 shows a perspective view of an alternative of a pin intended to cooperate with the prosthetic sternum device with manubrium according to the invention.

FIG. 7 shows a perspective view of one particular embodiment of a pin intended to cooperate with the prosthetic sternum device with manubrium according to the invention.

DETAILED DESCRIPTION OF THE INVENTION

Figure 1:
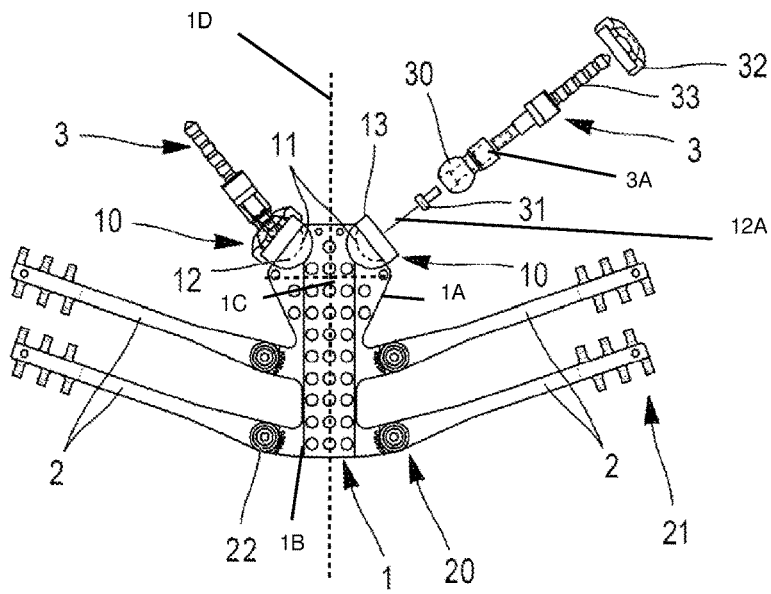
FIG. 1 shows a partially exploded planar view of the prosthetic sternum device with manubrium according to the invention.
Figure 2:
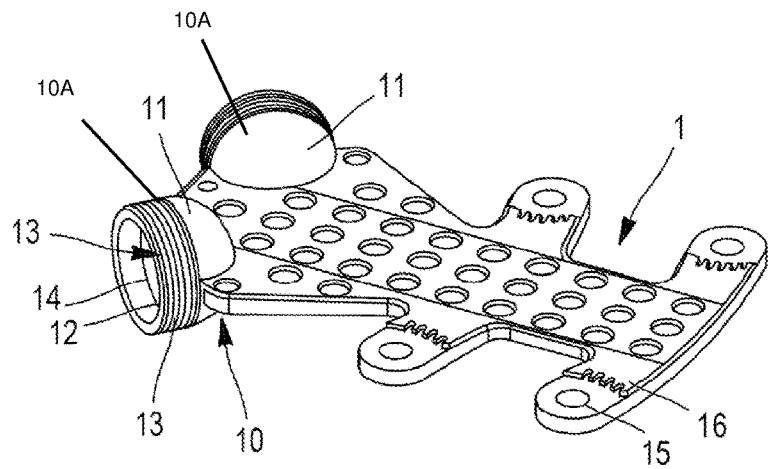
FIG. 2 shows a perspective schematic view of part of the same device.
Figure 3:
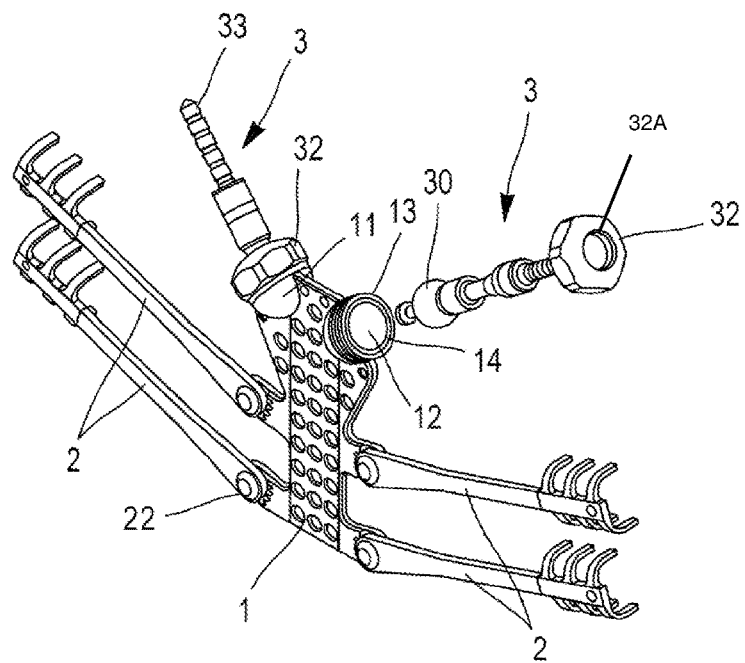
FIG. 3 shows an exploded perspective view of the same device.

In reference to FIGS. 1, 2 and 3, one can see that a prosthetic sternum device with manubrium according to the invention comprises, in this embodiment, a plate 1 having an upper portion 1A and a lower portion 1B opposite said upper portion so as to form a plate plane 1C with a longitudinal plate axis 1D and four means 2 for attaching to a rib or a plurality of attachment means 2, in a manner known in itself according to document FR 3,004,337, which extend laterally on either side of the plate 1.

It will be noted that according to document FR 3,004,337, each of the attachment means 2 includes an elongated piece 20 with a fastener 22 at one end for securing to the plate 1 and a hook 21 at an opposite end. The hook 21 is a means for attaching to a rib. The elongated piece 20 includes a hole, not visible in the figures, traversed by a screw as fastener 22 screwed into one of the tapped holes 15 included by the plate 1. Furthermore, an indexing means makes it possible to immobilize each attachment means 2 angularly; it is made up on the one hand, at each of the tapped holes, of a rack 16 arranged in an arc of circle concentric to the tapped hole 15, and on the other hand, by a finger 23 included by the end 20 of each of the attaching means 2 extending radially to the passage holes the screw 22, and intended to cooperate with one of the notches of the rack 16.

According to the invention, the plate 1 also includes, in its upper portion 1A, i.e., in the extreme part opposite the part that bears the attachment means 2, two insertion slots as securing means 10. Each securing means 10 has a corresponding pin 3 intended to be connected, by insertion of a diaphyseal nail 33 into a clavicle, not shown, after resection, said clavicle also being able to be prosthetic.

Each slot or securing means 10 is a polyaxial articulation 10A, being comprised of an extension 11 with a hemispherical cavity 12, with a cavity axis 12A passing through the plate plane 1C of the plate 1 and forming an angle with the main longitudinal axis of said plate 1, so as to open outwardly, upwardly and laterally. The extension is provided, on its distal edge and peripherally, with a thread 13.

The cavity 12 is intended to receive a spherical head 30 that is maintained therein by a nut or cover 32 screwed on the thread 13, the assembly forming a polyaxial articulation of the ball and socket type.

The pin 3 is intended to be secured to the polyaxial articulation through opening 32A on the cover 32, and to that end, its end, intended to be secured to the plate 1, and the spherical head 30 are assembled and maintained by a screw 31.

In the illustrated embodiment, the pin 3 is secured to the polyaxial articulation formed by the extension 11, the spherical cavity 12, the nut or cover 32 and the spherical head 30, but it is entirely possible to consider that the spherical head 30 is an integral part of the pin 30, and that consequently, the pin 3 includes part of the polyaxial articulation.

It should preferably be noted that each extension 11 is inwardly lined with an insert 14, which includes the cavity 12. Advantageously, the outer wall of the insert 14 is spherical, and the housing, not shown, of the latter made in the extension 11 is congruent thereto, so as to create an additional ball and socket connection between the insert 14 and the extension 11.

It will also be noted that the insert 14 and the spherical ball and socket joint 30 are made, non-limitingly, from PEEK (polyether ether ketone).

FIG. 4 shows an alternative of the prosthetic device according to the invention that differs from that shown in FIGS. 1, 2 and 3 in that the securing of the attachment means 2 to the plate 1 is done through sliding elements 17, to each of which a attachment means 2 is secured, and able to move and be blocked in one of the two slide channels 18 included by the plate 1, and arranged longitudinally on either side of a longitudinal axis XX'.

Associating the adjustment of the position of the attachment means 2 on the plate 1 and the multidirectional orientation of the pins 3 makes it possible to find very precise positioning of the prosthetic sternum device with manubrium according to the invention.

FIG. 4 shows an alternative of the prosthetic device according to the invention, where the plate 1 includes a number of tapped holes 15 for fastening to the catching means 2 greater than the number of attachment means 2 to be secured, so as to make it possible to choose the tapped holes 15 that are most appropriate for the anatomy of the patient.

FIG. 6 shows the pin 3 comprising a diaphyseal nail 33, a spherical head 30 and a nut or cover 32, as well as a small pin plate 34 that extends parallel to the diaphyseal nail 33 across and at a certain distance from the latter so as to be able, after insertion of the diaphyseal nail 33 into the clavicle, to come outwardly into contact with said clavicle. The small pin plate 34 is pierced with pin holes 35 allowing the passage of screws 36, only one of which is shown, intended to be screwed into the bone.

FIG. 7 shows part 36 of an alternative of the pin 3, which includes a threaded barrel 37 intended to be screwed into a spherical head, not shown, extended by three parallel rods 38 distributed in a triangle around a central axis 38A, and intended to be inserted in the clavicle, and which make up the diaphyseal nail.

We claim:

1. A prosthetic sternum device with manubrium, comprising:
   a plate having an upper portion and a lower portion opposite said upper portion so as to form a plate plane with a longitudinal plate axis,
   wherein said plate is comprised of two securing means attached to said upper portion; and
   a plurality of attachment means connected to said plate, wherein each attachment means comprises an elongated piece having a fastener at one end and a hook at an opposite end, wherein each securing means comprises a polyaxial articulation, wherein said plate is further comprised of a plurality of fastening holes, and wherein a number of fastening holes is greater than a number of said attachment means.

2. The prosthetic sternum device, according to claim 1, further comprising:

two pins, each pin being secured to a respective polyaxial articulation.

3. The prosthetic sternum device, according to claim 1, wherein at least one polyaxial articulation is comprised of a ball and socket joint.

4. The prosthetic sternum device, according to claim 2, wherein each pin has one pin end secured to a respective polyaxial articulation.

5. The prosthetic sternum device, according to claim 2, wherein at least one polyaxial articulation comprises:

an extension protruding from said plate so as to form a hemispherical cavity with a cavity axis passing through said plate plane and forming an angle with said longitudinal plate axis;

a cover being removably engaged to said extension and having an opening; and a spherical head housed in said hemispherical cavity and said cover, wherein a respective pin is extended through said opening and is attached to said spherical head.

6. The prosthetic sternum device, according to claim 5, wherein said at least one polyaxial articulation further comprises an insert, said insert lining said hemispherical cavity.

7. The prosthetic sternum device, according to claim 6, wherein said insert is comprised of polyether ether ketone, and wherein said spherical head is comprised of polyether ether ketone.

8. The prosthetic sternum device, according to claim 5, wherein said insert is spherical and concentric to said hemisphere cavity, said extension being partially spherical so as to form a ball and socket connection between said spherical head and said plate.

9. The prosthetic sternum device, according to claim 2, wherein each pin comprises a diaphyseal nail and a pin plate, said pin plate extending parallel, across, and spaced at a distance to said diaphyseal nail and having at least one pin hole for threaded engagement with a corresponding screw.

10. The prosthetic sternum device, according to claim 9, wherein said diaphyseal nail is comprised of three parallel rods arranged around a central axis.

11. A prosthetic sternum device with manubrium, comprising:

a plate having an upper portion and a lower portion opposite said upper portion so as to form a plate plane with a longitudinal plate axis, wherein said plate is comprised of two securing means attached to said upper portion; and a plurality of attachment means connected to said plate, wherein each attachment means comprises an elongated piece having a fastener at one end and a hook at an opposite end, wherein each securing means comprises a polyaxial articulation, wherein said plate is further comprised of two slide channels arranged longitudinally on either side of said longitudinal plate axis; and a plurality of sliding elements slidably engaged to a respective slide channel, and wherein each sliding element is attached to a respective fastener of a respective elongated piece.

12. A prosthetic sternum device with manubrium, comprising:

a plate having an upper portion and a lower portion opposite said upper portion so as to form a plate plane with a longitudinal plate axis, wherein said plate is comprised of two securing means attached to said upper portion;

a plurality of attachment means connected to said plate, wherein each attachment means comprises an elongated piece having a fastener at one end and a hook at an opposite end, and wherein each securing means comprises a polyaxial articulation; and two pins, each pin being secured to a respective polyaxial articulation, wherein at least one polyaxial articulations comprises:

an extension protruding from said plate so as to form a hemispherical cavity with a cavity axis passing through said plate plane and forming an angle with said longitudinal plate axis;

a cover being removably engaged to said extension and having an opening; and a spherical head housed in said hemispherical cavity and said cover, and wherein a respective pin is extended through said opening and is attached to said spherical head.

\* \* \* \* \*